Figure 1:
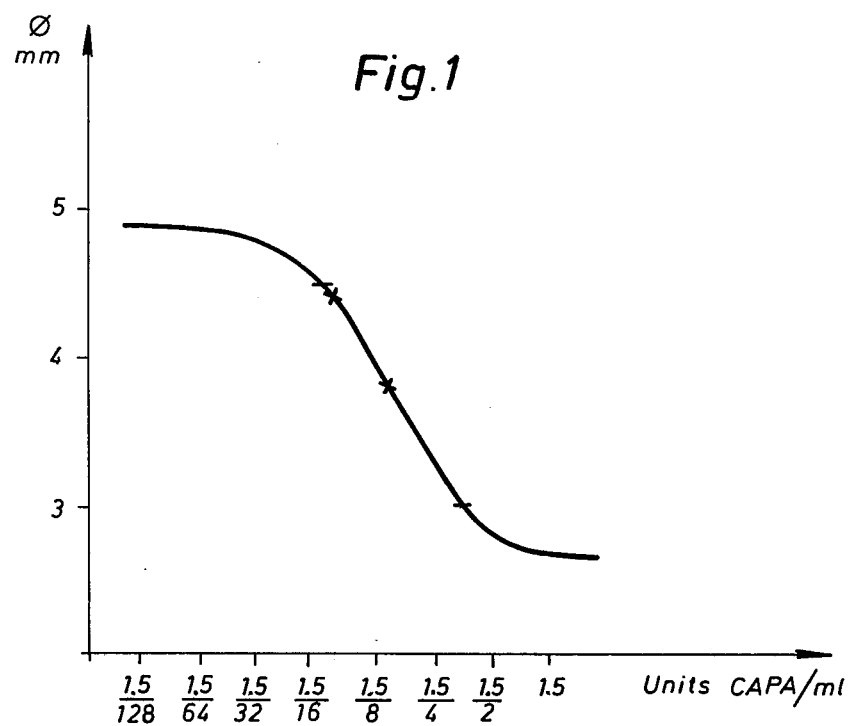

[19] United States Patent
Björklund

[11] 4,193,981
[45] Mar. 18, 1980

[54] PROCESS FOR QUANTITATIVE DETERMINATION OF CAPA ANTIGEN OR ANTIBODY

[75] Inventor: Tom B. Björklund, Bromma, Sweden

[73] Assignee: AB Bonnierföretagen, Sweden

[21] Appl. No.: 837,082

[22] Filed: Sep. 28, 1977

[30] Foreign Application Priority Data

Oct. 1, 1976 [SE] Sweden ............................ 7610939

[51] Int. Cl.$^2$ ..................... G01N 31/00; G01N 31/02; G01N 33/16
[52] U.S. Cl. ................................. 424/12; 23/230 B; 424/8; 424/11; 424/13
[58] Field of Search .................... 424/8, 11, 12, 13; 23/230 B

[56] References Cited
PUBLICATIONS

Kwapinski, Methodology of Immunochem. & Immuno Res., John Wiley & Sons, N.Y. 1972, p. 219.
Weir, Handbook of Exptl. Immuno., Blackwell Sci. Pub. London, 2nd Ed., 1973, pp. 20.13, 30.37.
Dunsford & Bowley, Techniques in Blood Banking, Oliver & Boyd Pub. London, 1955, p. 117 & FIG. 17.
Williams et al., Methods in Immunol. & Immunochem., Acd. Press, N.Y., vol. III, 1971, pp. 152, 168–163, 213–220.
Prolifigen Test Kit, Flyer 6 pages, copyright Bonnier Group, Stockholm, Apr. 12, 1976.

*Primary Examiner*—Anna P. Fagelson
*Attorney, Agent, or Firm*—Gordon W. Hueschen

[57] ABSTRACT

A process for quantitative determination of the amount of antigen in a solution while using hemagglutination inhibition technique, comprising preparing under serial dilution a series of samples of said solution, adding to each of said samples a predetermined amount of antiserum containing antibodies specific with regard to the antigen in question, adding after incubation to each of the resulting samples a predetermined amount of the antigen carried by a particulate carrier resulting in hemagglutination, and preparing a corresponding series of control samples with known decreasing amounts of antigen. By measuring the diameter of the hemagglutination deposits of the control samples and plotting the measured diameters against the antigen concentrations, an S-shaped curve is obtained, the middle part of which has a steep inclination. By selecting a sample in said series of samples of unknown antigen concentration with a diameter lying within said middle part of the curve, and by means of said diameter, the antigen concentration corresponding thereto can be determined from the curve. Antibody can be measured in a corresponding manner using direct hemagglutination.

6 Claims, 2 Drawing Figures

PROCESS FOR QUANTITATIVE DETERMINATION OF CAPA ANTIGEN OR ANTIBODY

The present invention relates to a process for quantitative determination of the amount of antigen or antibody in solution while using so-called indirect or direct hemagglutination technique.

In brief, the present invention, according to one aspect thereof, is based upon a modification of the classical hemagglutination inhibition reaction, in which antigen in a sample inhibits the ability of anti serum to agglutinate red cells labelled with antigen. The technique hitherto used for determination of antigen, for example for cancer diagnosis, is based on the use of blood cells labelled with antigen which are allowed to react with a constant quantity of antibodies and a stepwise decreasing concentration of antigen. After incubation there is added to each of the resulting mixtures of antigen and antibodies a suspension of red cells labelled with the same antigen, hemagglutination being obtained, more particularly an increasing hemagglutination reaction by decreasing quantities of antigen in the initial antigen solution added to antiserum. Now, when the corresponding procedure is performed with an antigen solution of unknown concentration of antigen there is obtained a corresponding series of samples of increasing hemagglutination, and when comparing series of known antigen concentrations and series of unknown antigen concentrations it is possible qualitatively to indicate the presence of antigen in the unknown sample and possibly to obtain a semiquantitative determination of the antigen concentration.

Since an accurate determination of the antigen concentration in an unknown sample is of a great importance, inter alia in cancer diagnosis based on the presence of human cancer antigen in for example the blood, it is desirable to find a simple and reliable method for quantitative determination of the concentration of antigen in solution. The present invention has for its purpose to provide such a process for quantitative determination of antigen. It is of importance that such a process can be based on simple analyzing methods without using complicated equipment such as used in for example so-called radioimmunoassay.

In connection with the instant invention it has been found that if, in association with the hemagglutination pattern obtained in the above presented serial dilution and reaction between antigen and antibody, the diameters of the deposits are measured and plotted in a diagram as a function of the antigen concentrations, in the solutions, an S-shaped curve is obtained whose intermediary or middle part around the inflexion point has a steep inclination. Thus, this means that even if the diameters cannot be recorded with a particularly high degree of accuracy the accuracy of the red antigen concentration still is surprisingly high. The fact that plotting the diameters of the hemagglutination deposits as a function of the logarithm of the antigen concentration would result in an S-shaped curve was wholly surprising and one would in fact have expected an approximately linear function.

In the process of this invention for quantitative determination of the amount of antigen in a solution there is thus prepared, under serial dilution, a series of samples of said solution of decreasing antigen concentration, and to said samples there is then added a predetermined amount of antiserum containing antibodies specific with regard to the antigen in question. To each of the resulting samples there is then added, after incubation, a predetermined amount of the antigen carried by a particulate carrier, hemagglutination taking place in an extent corresponding to the amount of accessible antibody. Then there is prepared a corresponding series of control samples of known decreasing amounts of antigen. The invention is characterized by measuring the diameter of the hemagglutination deposits of the control samples and plotting the measured values of the diameters against the logarithm of the antigen concentrations, to give an S-shaped curve, the middle part of which including the inflexion point having a steep inclination. Then there is selected a sample of said series of samples containing unknown quantities of antigen having a diameter lying within said middle part of the curve, by means of which the antigen concentration corresponding to the last-mentioned diameter is observed. In view of the fact that said middle part of the curve has a steep inclination there is obtained an accurate measure of the antigen concentration of the corresponding sample in spite of the fact that the reading of the plotted diameter of the hemagglutinate cannot be made with an accuracy better than about ±0.05 mm.

In other words, the steps performed by the process of this invention for quantitative determination of the amount of antigen in a solution are the following:

(1) measuring the diameter of the hemagglutination deposits of the control samples and
(2) plotting the measured diameters against the antigen concentrations to give an S-shaped curve, the middle part of which has a steep inclination,
(3) selecting a sample in said series of samples of unknown antigen concentration having a known diameter lying within said middle part of the curve,
(4) comparing said known diameter of the unknown sample with the diameters of samples of known concentration as plotted against known diameter in step (2), and
(5) reading off the antigen concentration corresponding to the known diameter of said unknown sample.

In a preferred embodiment of the process of the invention the diameter is measured also for a sample adjacent to said selected sample, the antigen concentration of which has been determined, in view of which by knowing the antigen concentration ratio between said two samples and by means of the curve obtained the accuracy of the analysis can be verified by recording the second diameter measured in the diagram, whereby if everything is in order the last-mentioned recording should lie on or close to the curve.

The technique of this invention is generally applicable on all kinds of hemagglutination procedures, for example determination of albumen or protein antigens, but the invention will in the following be illustrated with reference to a particular cancer associated polypeptide antigen, in the following called CAPA.

The present invention is, of course, applicable also on so-called direct hemagglutination technique, by which the amount of antibody in a solution can be determined in a corresponding manner. In this case a series of samples of an antibody solution is prepared, and to each of the resulting samples there is added a predetermined amount of an antigen reacting specifically with the antibody in question and carried by a particulate carrier, resulting in hemagglutination. Moreover there is prepared a corresponding series of control samples of known decreasing amounts of antibody. Now, if the diameter of the hemagglutination deposits of the control samples is plotted as a function of the antibody concentration there is obtained a curve of reversed S-shape, the middle part of which including an inflextion point has a steep inclination in the same way as that obtained by the hemagglutination inhibition technique. This reversed S-curve results in the same advantages from the point of view of recording as the S-curve hereinbefore described.

Accordingly, the steps to be performed by using the so-called direct hemagglutination technique in accordance with this invention are the following:

(1) measuring the diameter of the hemagglutination deposits of the control samples and (2) plotting the measured diameters as a function of the antibody concentrations to give a curve of reversed S-shape, the middle part of which has a steep inclination, (3) selecting a sample in said series of samples of unknown antibody concentration having a known diameter lying within said middle part of the curve, (4) comparing said known diameter of the unknown sample with the diameters of samples of known concentration as plotted against known diameter in step (2), and (5) reading off the antibody concentration corresponding to the known diameter of said unknown sample.

As a particulate carrier for the antigen there may advantageously be used red blood cells, particularly sheep red cells, but also latex, bentonite or collodium are fully conceivable as carriers.

Figure 2:
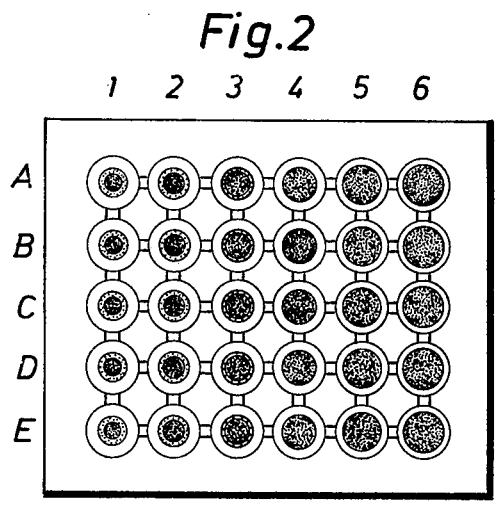

The present invention will be further described by an example in connection with the appended drawing showing a diagram in FIG. 1 on the diameters of hemagglutination deposits as a function of the logarithms of the antigen concentrations, whereas FIG. 2 shows a photographic recording of a standard series of hemagglutination reactions.

EXAMPLE

The material CAPA used in the following is the material prepared in accordance with Example I of U.S. patent Ser. No. 3,960.827. Thus, said material is a polypeptide characteristic for human cancer.

Preparation of CAPA-albumen complex

An aliquot of the CAPA as prepared under Example 1 according to the above-identified U.S. patent is dissolved in formic acid (for instance 0.05 M; the pH should be within the range 2-3). A clear solution is obtained. To said solution there is added albumen powder or a solution of albumen at the same pH as of the above formic acid solution (200 parts by weight of albumen per 1 part by weight of CAPA) resulting in a clear solution of CAPA and albumen. Then the pH of the solution is slowly increased by adding a base (for instance an aqueous sodium hydroxide solution or ammonia) until pH reaches about 7.5. This results in a clear solution containing CAPA and albumen in the form of a complex.

This solution containing 12 µg CAPA/ml may be used. directly in the diagnostic procedure described below or the complex may be isolated in the form of a white powder by freeze-drying. The powder is stable in the cold (+4° C.) for a long period of time.

It has been shown by experiments that maximum utilization of the CAPA activity is obtained at a weight ratio of albumen to CAPA equal to about or exceeding 200:1.

Preparation of tanned and labelled red blood cells

Fresh sheep blood (1 part by volume) are added to sterile Alsever's solution (1.2 part by volume) (Alsever's solution is prepared from 250 g glucose, 80 g sodium citrate dihydrate, 42 g NaCl, add water to make up to 10 liters, pH adjusted to 6.1 with 10% citric acid monohydrate). The mixture is centrifuged and the red blood cells are resuspended once in Alsever's solution and twice in a buffer solution of pH 6.8. Finally, a suspension of the red blood cells is made up in the buffer 6.8 at a concentration of $10^9$ cells/ml.

1 volume of red blood cell suspension prepared as above is added to 1 volume of buffer solution of pH 6.8 containing about 18 µg tannic acid/ml under stirring. The thus tanned red blood cells are centrifuged and resuspended twice in buffer of pH 7.5. Finally, the red blood cells are suspended in buffer of pH 7.5 at a concentration of $10^9$ cells/ml.

An aliquot of the CAPA complex prepared under Example Ib above is dissolved in a buffer solution of pH 7.5 to give a concentration of 3 µg CAPA per ml (calculated on pure CAPA). 1 part by volume of the suspension of tanned red blood cells prepared above is added dropwise at 0° C. to 1 part by volume of the CAPA complex solution for a period of time of 10 minutes. The labelled cells are centrifuged and resuspended in a buffer solution of pH 7.5 containing a stabilizing amount (about 1.2 volume/volume) of inert human serum to give a suspension containing $1.6 \times 10^8$ labelled cells per ml. These labelled cells are used as shown below in the diagnostic procedure of the invention.

Preparation of antibodies

In view of the fact that the CAPA denaturates irreversibly at neutral pHs, parenteral injection of the polypeptide does not result in the production of antibodies. In order to be able to transfer the polypeptide in an active condition to the antibody producing cells it is necessary to maintain the polypeptide in the solution at pHs lower than about 3 (0.02 m HCOOH, pH 2.8) and to emulgate the solution in oil to the formation of extremely small drops surrounded by a protecting oil layer. The injection of the emulsion resulted in production of satisfactory quantities of antibodies, which reacted specifically with the CAPA in hemagglutination reactions, wherein blood cells had been labelled with CAPA.

Preparation of immunizing agent 816 micrograms of pure CAPA prepared from pooled human cancer tumors were dissolved in 1.0 ml of 0.02 m HCOOH of pH 2.8. To the resulting solution there was added dropwise 1.0 ml adjuvant oil (commercial preparation from Difco Laboratories, Detroit, Michigan, USA; Bacto-Adjuvant, Freund) under simultaneous emulsification. The emulsification was carried out according to Freund by means of an injection syringe, the mixture being drawn up and down in the syringe to the formation of a uniform, white emulsion having about the same consistency as wipped cream. One drop of said emulsion was tested with ice water to confirm that it floated separately and maintained intact.

The resulting, semi-liquid emulsion was used for subcutaneous and intramuscular injections on rabbits.

Immunization of five rabbits

In the first injection a so-called complete adjuvant was used and in the subsequent injections a so-called incomplete adjuvant was used. After initial drain of blood from each of five rabbits to establish 0-values, totally 408 micrograms of emulsified CAPA at pH 2.8 were injected subcutaneously on each right and left hand side. At ten days intervals additionally three injections were given, the first one intramuscularly in each hind leg and the second and the third subcutaneously on both front sides and both backs, respectively. The selection of the injection sites was made in order to utilize the admission areas of the regional lymphatic glands. In total, each rabbit received about 1.6 mgs of CAPA in the form of emulsion. 14 and 24 days after the last injection test samples of blood were taken, which were subjected to hemagglutination analysis with regard to the presence of specific antibodies against CAPA. Two days after the last sample a maximum amount of blood was drained, which was recovered in the form of serum that was sterile filtered and transferred in small portions to sterile tubes. These tubes could be stored in the cold while maintaining the specificity.

Diagnostic procedure

As indicated earlier the analysis technique according to the instant invention is based on indication of the existence of CAPA by means of a modified hemagglutination inhibition technique (micro method). In principal, the following procedure is used:

25 $\mu$l of patient serum and standardized CAPA-preparation, both of which had been absorbed with sheep red cells, are titrated in 8-step two-dilution in Linbro IS-MRC-96-dilution plates, and then 25 $\mu$l specific antiserum in limit dilution (about 1:2000) is added to eacy cavity. After incubation at 22° C. for 10 minutes there are added to each cavity 50 $\mu$l of a suspension of about 6 to 8,000,000 sheep blood red cells tanned and labelled with isolated CAPA linked to human albumen as shown above (about 2-4 micrograms per $10^9$ blood cells).

As antiserum there was used horse anti-HeLa from 19 November, 1962, absorbed by normal tissues and pooled human serum. The immunization was made with washed fragments of HeLa-cells grown in Eagle's medium containing 20% inactivated human serum in flat glass bottles. The cells had been harvested with EDTA, centrifuged and washed three times with water.

In the presence of CAPA in serum the horse antibodies are neutralized resulting in the absence of agglutination when the polypeptide labelled blood cells are subsequently added. The dilution plates containing the hemagglutination deposits are then photographed, which also means a practical way for future documentation of the experimental results, and the diameters of the deposits are measured, suitably by using a so-called measuring magnifying glass having a measuring scale built into the optics. In the table I below there are given the diameters obtained when reading off a standard plate which has been photographed. In the table there is given also the average of the five rows of cavities.

Table I.

| Cavity<br>U CAPA/ml | 1<br>1.5 | 2<br>0.75 | 3<br>0.375 | 4<br>0.1875 | 5<br>0.0937 | 6<br>0.0468 | 7<br>0.0234 | 8<br>0.0117 |
|---|---|---|---|---|---|---|---|---|
| A Row 1 | 2.7 | 2.8 | 3.3 | 3.9 | 4.5 | 4.8 | 4.9 | 4.9 |
| B Row 2 | 2.7 | 2.9 | 3.3 | 3.8 | 4.5 | 4.7 | 4.8 | 4.8 |
| C Row 3 | 2.7 | 2.9 | 3.3 | 3.9 | 4.4 | 4.7 | 4.8 | 4.8 |
| D Row 4 | 2.7 | 2.9 | 3.3 | 3.9 | 4.4 | 4.7 | 4.8 | 4.8 |
| E Row 5 | 2.7 | 2.9 | 3.3 | 3.9 | 4.4 | 4.7 | 4.8 | 4.8 |
| $\overline{C}$ diam. | 2.7 | 2.88 | 3.3 | 3.88 | 4.44 | 4.72 | 4.82 | 4.82 |

In FIG. 2 of the appended drawing there is shown a photographic reproduction of the hemagglutination tests presented in the above table I. By means of this photographic reproduction it is easy, for example by means of a measuring magnifying glass with a built-in measuring scale to read the diameters of the hemagglutination deposits and then plot same in a diagram with the diameters as a function of the logarithms of the antigen concentrations.

In FIG. 1 of the appended drawing there is shown in the form of a diagram the average diameters plotted against the logarithm of the CAPA-concentration. As is clear from the diagram the curve obtained has S-shape, and the area suitable for measurements is the middle part of the curve, i.e. the area between about 3 and about 4.5 mms, within which area the CAPA-concentration corresponding to a certain diameter can be read off with a high degree of accuracy.

By corresponding serial dilution and hemagglutination of an unknown sample it is necessary only to select a diameter lying within said part of the curve and to read off the corresponding CAPA-concentration. For the purpose of control a further sample may be selected lying immediately above or immediately below the first plotted diameter of the unknown sample, and by the knowledge of the CAPA-concentration for said other sample which is either doubled or halved it is possible by plotting on the curve to see if said second sample corresponds to the expected concentration. In this way double control of the accuracy of the analysis will be obtained.

As an example of such measurement of an unknown sample there are given in the table II below corresponding measured diameters and the average values thereof. Only the diameters of three concentrations have been measured, all lying within the area of the curve of FIG. 1 indicated between horizontal lines.

Table II.

| Row 1 | 3.8 | 4.4 | 4.7 |
|---|---|---|---|
| Row 2 | 4.0 | 4.4 | 4.7 |
| Row 3 | 3.8 | 4.4 | 4.7 |
| Row 4 | 3.8 | 4.4 | 4.7 |
| Row 5 | 3.8 | 4.4 | 4.7 |
| $\overline{C}$ $\phi$ | 3.84 | 4.4 | 4.7 |

Now, if the average diameter value 4.4 is selected and plotted in the diagram of FIG. 1 (indicated by a cross) there is obtained on the horizontal axis the concentration of the antigen in units per milliliter. As a check an adjacent diameter value corresponding to double the antigen concentration can be indicated (also indicated with a cross in the diagram), whereby with knowledge about the concentration in relation to the first plotted point the accuracy of the analysis may be controlled, since if accuracy is the case the second plotted cross will lie on the curve.

In the present example there is used as a concentration measure micrograms of CAPA per milliliter on the one hand, and in the table U per milliliter on the other hand, which latter symbol means unit per milliliter. The relationship between said two ways of expressing the concentration of antigen in solution is that about 3 units correspond to 1 microgram of antigen in the purified form as per the instant example.

With the accuracy made possible by the technique of this invention with regard to determination of the concentration of an antigen in solution, it is of utmost importance that the serial dilution carried out in connection with applying the technique takes place with a sufficiently high degree of accuracy.

In order to obtain such accuracy in the serial dilution it has been found particularly suitable to use the dispensing and pipetting/titration equipment described in the two U.S. patent Ser. Nos. 3,990,313 and 3,998,103.

In the technique of this invention which is thus based upon hemagglutination technique, both direct and indirect hemagglutination wherein in a manner known per se antigen reacts with antibody, it is, in order to obtain maximum sensitivity in the analysis, suitable to choose a concentration of antibody lying somewhat below that required for complete agglutination of antigen-labelled blood cells. Thus, it seems as though excess of antibody interferes with the sensitivity of the analysis.

As indicated earlier, it is possible within a certain concentration range, namely that for which corresponding diameters rapidly increase at increasing concentration, i.e. within the middle part of the curve of FIG. 1, to determine with a high degree of accuracy the concentration of the sample by reading the diameter, this being so in view of the fact that a small error in the reading of the diameter still results in a high degree of accuracy with regard to the determination of concentration. Within the concentration range, in which the diameter does increase only slowly by increasing concentration, a very little error in the diameter reading results in a too large error in the determination of the concentration. The problem hereby arising may be simply dissolved at low concentrations by subjecting the sample to serial dilution so that its concentration comes within the concentration range corresponding to the middle part of the curve. Such dilution is a routine measure to one skilled in the art and enables in a simple manner utilizing the previously indicated advantages in the relation between diameter and concentration.

What is claimed is:

1. In a process for quantitative determination of the amount of CAPA, cancer associated polypeptide antigen, in a solution while using agglutination inhibition technique, comprising preparing under serial dilution a series of samples of said solution, adding to each of said samples a predetermined amount of antiserum containing antibodies specific with regard to the CAPA, adding after incubation to each of the resulting samples a predetermined amount of the said antigen carried by a particulate carrier resulting in agglutination, and preparing a corresponding series of control samples with known decreasing amounts of said antigen, the steps of
   (1) measuring the diameter of the agglutination deposits of the control samples and
   (2) plotting the measured diameters against the antigen concentrations, thereby obtaining an S-shaped curve, the middle part of which has a steep inclination,
   (3) selecting a sample in said series of samples of unknown antigen concentration having a known diameter lying within said middle part of the curve,
   (4) comparing said known diameter of the unknown sample with the diameters of samples of known concentration as plotted against known diameter in step (2), and
   (5) reading off the CAPA concentration corresponding to the known diameter of said unknown sample.

2. A process according to claim 1, including the step of measuring the diameter for a sample lying adjacent to said sample, the CAPA concentration of which has been determined, whereby with knowledge about the CAPA concentration ratio between said samples and the curve it is possible by plotting on the curve to check the accuracy of the analysis.

3. A process according to claim 1, wherein the particulate carrier for the said antigen is red blood cells, latex, bentonite or collodium.

4. A process according to claim 1, including the step of photographing the agglutination deposits and measuring the diameters on the photographs hereby obtained with a measuring magnifying glass.

5. A process according to claim 1, including the steps of plotting the diameter values obtained against the logarithms of the said antigen concentrations.

6. In a process for quantitative determination of the amount of CAPA, cancer associated polypeptide antigen, antibody in solution while using agglutination technique, comprising preparing under serial dilution a series of samples of said solution, adding to each of said samples a predetermined amount of CAPA reacting specifically with said antibody and carried by a particulate carrier resulting in agglutination, and preparing a corresponding series of control samples with known decreasing amounts of said antigen, the steps of (1) measuring the diameter of the agglutination deposits of the control samples and (2) plotting the measured diameters as a function of the antibody concentrations, thereby obtaining a curve of reversed S-shape, the middle part of which has a steep inclination, (3) selecting a sample in said series of samples of unknown antibody concentration having a known diameter lying within said middle part of the curve, (4) comparing said known diameter of the unknown sample with the diameters of samples of known concentration as plotted against known diameter in step (2), and (5) reading off the antibody concentration corresponding to the known diameter of said unknown sample.

* * * * *

UNITED STATES PATENT AND TRADEMARK OFFICE
CERTIFICATE OF CORRECTION

PATENT NO. : 4,193,981

DATED : March 18, 1980

INVENTOR(S) : Tom B. Björklund

It is certified that error appears in the above—identified patent and that said Letters Patent is hereby corrected as shown below:

[56] PUBLICATIONS, line 8; "168-163," should read -- 168-174, -- Notice of References Cited, Attachment to paper No. 4, Other References, line 4.
Col. 3, lines 5&6; "inflextion" should read -- inflexion --
Col. 3, line 46; "3,960.827." should read -- 3,960,827. --
Col. 3, line 65; "used. directly" delete the period (.).
Col. 4, line 66; "wipped" should read -- whipped --
Col. 7, line 22; "patent" should read -- patents --
Col. 8, line 35; "steps" should read -- step -- Response and Amendment dated September 20, 1978, page 1.

Signed and Sealed this

Nineteenth Day of August 1980

[SEAL]

Attest:

SIDNEY A. DIAMOND

Attesting Officer

Commissioner of Patents and Trademarks